United States Patent [19]

Fléche et al.

[11] 4,339,387

[45] Jul. 13, 1982

[54] PROCESS FOR MANUFACTURING 5-HYDROXYMETHYLFURFURAL

[75] Inventors: Guy Fléche, Merville; Antoine Gaset, Toulouse; Jean-Pierre Gorrichon, Toulouse; Eric Truchot, Toulouse; Philippe Sicard, Lille, all of France

[73] Assignee: Roquette Freres, Lestrem, France

[21] Appl. No.: 181,744

[22] Filed: Aug. 27, 1980

[30] Foreign Application Priority Data

Sep. 5, 1979 [FR] France .................. 79 22251

[51] Int. Cl.$^3$ ............................. C07D 307/46
[52] U.S. Cl. .................................. 549/488
[58] Field of Search ........................ 260/347.8

[56] References Cited

U.S. PATENT DOCUMENTS

| 2,750,394 | 6/1956 | Peniston | 260/347.8 |
| 3,071,599 | 1/1963 | Hales et al. | 260/347.8 |
| 3,118,912 | 1/1964 | Smith | 260/347.8 |

FOREIGN PATENT DOCUMENTS 54-154757 12/1979 Japan .

OTHER PUBLICATIONS

Schraufnagel et al., Chemical Abstracts, vol. 82 (1975) 98278n, p. 464.
Techniques of Chemistry, Organic Solvents, vol. II, 3. Edition, pp. 1–19.
Bull. Chem. Soc. Jpn. 53 (1980), pp. 3705–3706.

Primary Examiner—Richard Raymond
Attorney, Agent, or Firm—Larson & Taylor

[57] ABSTRACT

The invention relates to a process for manufacturing 5-hydroxymethylfurfural.

This process comprises decomposition of a hexose in a reaction medium constituted by water and an organic solvent, by heating to a temperature below 100° C., situated especially in the range from 70° to 95° C., in the presence of a solid catalytic support, especially an exchange resin with a cationic function.

5-hydroxymethylfurfural is applied in numerous syntheses.

10 Claims, No Drawings

PROCESS FOR MANUFACTURING 5-HYDROXYMETHYLFURFURAL

The invention relates to a process for manufacturing 5-hydroxymethylfurfural denoted below by HMF and whose formula is:

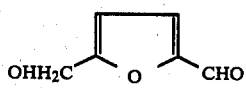

HMF has numerous applications, especially in the synthesis of dialdehydes, glycols, ethers, aminoalcohols and acetals, and other organic intermediates which can lead to the production of numerous chemical products such as solvents, surface-active agents, phytosanitary products, resins and the like.

HMF is a decomposition product of hexoses with 6 carbon atoms.

The decomposition of these sugars is executed in an acid medium and by the action of heart. It is characterised by a dehydration followed by ring formation.

The hexoses comprise the aldohexoses which have an aldehyde function and the ketohexoses which have a ketone function.

Among the aldohexoses, may be mentioned, for example, glucose, galactose, mannose, idose and, among the ketohexoses, fructose or levulose, sorbose, tagatose and allose.

More generally, any oligo- or polysaccharide whose decomposition leads to aldohexoses and/or ketohexoses may be used as a starting material for the invention.

The mechanism of formation of HMF is represented by the diagram indicated below. Under the effect of acid on the hexoses, intermediate products are formed whose structure is still very poorly known and which gives birth either to HMF, or to a group of compounds, called humins, which correspond to insoluble polymerisation products. According to the operating conditions, the development of the intermediates will be oriented towards the formation of HMF or towards that of humins.

HMF may itself lead to secondary products either by opening of the ring (levulinic acid and formic acid), or by polymerisation thereby furnishing products called hereafter humins.

Reaction diagram:

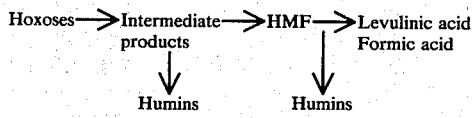

In general, high temperature and high acidity encourage the formation of mixtures of humins and of levulinic/formic acids to the detriment of the HMF.

In known processes for manufacturing HMF, temperatures equal to or higher than 100° C. are used; in certain cases, these temperatures may reach 300° C.

In these known processes, the yields are low and the side reactions important, the reaction medium being always contaminated with insoluble humins and/or levulinic acid.

It is a particular object of the invention to overcome these drawbacks and provide a process for manufacturing HMF having a better yield and leading to less impurities.

According to the process of the invention, the reaction of decomposition of the hexoses is carried out in a reaction medium constituted by a binary system comprising water and a solvent, by heating to a temperature below 100° C., situated especially in the range of 70° to 95° C., in the presence of a catalytic solid support, especially of an exchange resin with a cationic function.

According to a first advantageous embodiment of the abovesaid process, the reaction is carried out under a pressure higher than atmospheric pressure and which can reach 100 bars, this pressure being preferably selected within the range from 1 to 5 bars.

According to a second advantageous embodiment of the abovesaid process, recourse is had, as solvent associated with the water, to a solvent whose solubility in water is as low as possible, this solvent being selected from among those which constitute good solvents of HMF.

According to a third advantageous embodiment of the abovesaid process, the HMF formed is extracted continuously from the reaction medium by separating from the aqueous phase the organic solvent phase which has dissolved the HMF, recovering the latter from the organic phase and advantageously recirculating the latter into the reaction medium.

The invention relates also to a certain number of other features which are preferably used at the same time and which will be more explicitly considered in the complement of the description which follows relating to advantageous embodiments and by means of which it will be more easily understood.

The process according to the invention associates a heterogeneous catalysis carried out within an aqueous-organic reaction medium with an operation in a moderate range of temperature, and enables the HMF to be protected from the trouble-some effects of temperature by extracting it from the medium progressively with its formation.

The starting material utilised is advantageously a hexose.

Preferably, keto-sugars such as fructose or levulose very widely found in nature are used, as well as any systems capable of giving rise to the formation of this sugar in the reaction medium or in an appended device placed in series with the reactor. Thus, for example, a solution of dextrose could be isomerised and the thus-obtained dextrose-fructose mixture be treated under the reaction conditions of the invention.

The hexose is solubilised in the aqueous phase of the water-organic solvent system applied, and this at concentrations depending on the solubility of the sugar concerned. Thus, in the case of fructose, solutions having concentrations of 1500 g/l could be applied. Preferably, concentrations comprised between 100 and 500 g/l are selected.

The dehydration reaction occurs in the aqueous phase and the HMF produced initially in the water migrates to the organic solvent. There is hence a continuous transfer from the aqueous reaction phase to the organic recovery phase.

The organic solvent of the reaction medium is selected taking into account the following requirements:

it must be the least miscible possible with water at the temperatures of the reaction to produce two phases, it must be a good solvent of HMF.

It may be selected from among:

the ketones, especially methylisobutylketone and diethylketone, the nitriles, especially butyronitrile and benzonitrile, ethers, especially dichloroethylethers and dimethoxyethane, water-immiscible alcohols, the halogenated derivatives, especially chlorobenzene and dichlorobenzene, the aliphatic or aromatic hydrocarbons, saturated or not, especially xylene and nitroalkanes, especially nitromethane and nitropropane.

The proportions of the aqueous phase with respect to the organic phase are, preferably, from 1/7 to 1/12 by volume.

The dehydration reaction is applied at a temperature less than 100° C., preferably comprised between 70° and 95° C. and, more preferably again, comprised between 85° and 90° C., in the presence of a solid catalytic support, especially of a cationic exchange resin.

The recourse to the above-mentioned catalytic supports is advantageous from numerous points of view and eliminates any corrosion problems encountered in the processes of the prior art.

The resin constituting the catalyst may be a strong or weak cationic exchanger, in solid form, the functionalisation being preferably in the H+ form. By way of example, the resin known under the trademark "Amberlite C200" of the Rohm & Haas Company, and that known under the trademark "Lewatit SPC 108" of the Bayer Company, may be mentioned.

Preferably, highly acid resins are selected. The weak cationic resins bearing carboxylic groups give too low reaction speeds.

Other solid catalytic supports may also be used; thus, recourse may be had to solid supports based on silica, alumina or silica-alumina functionalised by acid groups, especially sulfonic groups; by way of example, that knownunder the trademark "Spherosil S" of the Rhône-Poulenc Company may be mentioned, which is constituted by silica beads functionalised at the surface by sulfonic groups; another example of a catalytic support is that knownunder the trademark "Nafion" of the DuPont de Nemours Company and which is constituted by a super acid resin constituted by a carbofluorinated polymer functionalised by sulfonic groups.

The amount of catalytic support applied is a function of the exchange power of the type concerned. This exchange power is expressed in meq (milliequivalent) per gram of support.

The amounts of support or more especially of resin are calculated according to their own characteristics so that the operation is carried out with a ratio:

0.1 < exchange capacity/weight of hexose < 100.

The exchange capacity is expressed in meq. It is equal to the product of the exchange power of the resin and the weight of the latter applied.

It is advantageous to carry out the process according to the invention at a pressure above normal.

To do this, a gaseous cushion may be used, constituted by air, hydrogen, nitrogen, helium or argon. Preferably, a gas will be selected which does not contain oxygen to avoid decomposition of the furane ring. Although no apparent increase in the yield is noted over a very wide range of pressure, from 1 to 50 bars, for reasons of ease of operation, a pressure comprised within the range from 1 to 5 bars is selected.

Operation under pressure enables the conversion speed to be accelerated; this is particularly advantageous to the extent that a high degree of conversion is sought whilst keeping the level of the by-products at the lowest possible value.

It is also advantageous to extract the HMF formed at regular intervals, even continuously.

To do this, the organic solvent in which the HMF is dissolved is recovered; it is possible, for this purpose, to collect the solvent by overflow, the organic phase being generally of lower density than the aqueous phase and accumulating as an easily separable upper layer. From this organic phase, the HMF is recovered by distillation and the solvent freed from its HMF is advantageously recirculated. This recycled solvent is injected by means of a pump into the aqueous phase to facilitate the passage of the HMF from the latter to the organic phase.

By means of extraction from the aqueous phase of the HMF formed progressively with the advance of the reaction, the formation of by-products from this product can be reduced to a value of almost nil.

The yield of the process according to the invention is excellent.

The invention will be still better understood by means of the Examples which follow.

EXAMPLE 1

Into a stainless steel reactor of 50 liters provided with a stirrer, under reflux column, is introduced 36 liters of methylisobutylketone. Then successively, 1 kg of crystallined levulose and 4 liters of water are added. With stirring, the levulose dissolves rapidly in the aqueous phase. 0.8 kg of cationic resin of the brand "Lewatit SPC 108" predried (or 1.6 kg of cationic resin of the brand "Lewatit" in the commercial form including 50% of water, but in this case, not more than 3.2 liters of water instead of 4 liters are introduced), are then introduced. The mixture with stirring is then brought rapidly to 89° C.; the temperature and the stirring are kept up for 5 hours. After this time, the reaction mixture is filtered, the resins are washed with the amount of water necessary to extract the products absorbed constituted by the HMF and the remaining levulose.

The aqueous and organic phases are separated. The aqueous phase includes the residual levulose as well as a little HMF ad levulinic acid.

The organic phase contains the HMF extracted as well as a small amount of levulinic acid.

The assays of the products of the reaction enable a balance sheet to be drawn up and to calculate:

the conversion ratio T expressed by the ratio $$\frac{\text{moles of HMF formed in the reaction}}{\text{moles of levulose introduced into the reactor}} \times 100$$

the yield R expressed by the ratio $$\frac{\text{moles of HMF formed outside of the reaction}}{\text{moles of levulose consumed by the reaction}} \times 100.$$

The foregoing experiment was repeated replacing the methylisobutylketone with equivalent volumetric amounts of:

diethylketone
butyronitrile
benzonitrile dichloroethylether
nitropropane.

Finally, to compare the results obtained with those produced by means of a purely aqueous system, the solvent is replaced by the water thus working in a single phase.

The results are brought together in Table I.

TABLE I

|  | Methyliso-butylketone | Diethyl-ketone | Butyro-nitrile | Benzo-nitrile | Dichloro-ethylether | Nitro-propane | Water |
|---|---|---|---|---|---|---|---|
| Levulose consumed / Levulose introduced % | 51 | 63 | 73 | 82 | 69 | 27 | 38 |
| HMF (g) | | | | | | | |
| aqueous phase | 56 | 56 | 40 | 232 | 64 | 92 | 38 |
| organic phase | 212 | 64 | 120 | 184 | 228 | 160 | — |
| Levulinic acid (g) | | | | | | | |
| aqueous phase | 0 | 0 | 0 | 0 | 0 | 0 | 20 |
| organic phase | 0 | 0 | 0 | 0 | 0 | 0 | — |
| Humins | 0 | 0 | 0 | 0 | 0 | 0 | very large amount |
| T % | 38 | 17 | 23 | 59 | 42 | 36 | 5 |
| R % | 74 | 27 | 31 | 73 | 61 | 54 | 15 |

These results establish the advantage in using the aqua-organic system according to the invention rather than simply an aqueous phase. In particular, the levels of humins and of levulinic acid are nil when a solvent according to the invention is employed.

EXAMPLE 2

The conditions were those of Example 1, using methylisobutylketone. Three experiments were carried out applying different catalysts:

| | |
|---|---|
| pre-dried cationic resin of the brand "Lewatit SPC 108" | 0.8 kg |
| catalytic support in the form of beads of the brand "Spherosil S" | 1.8 kg |
| super acid resin of the brand "Nafion" | 4.2 kg |

The amounts of resin or catalytic support are calculated so that the exchange capacity is identical for the three tests.

The temperature was fixed at 85° C. and the reaction time at 4 hours.

The results obtained are grouped in Table II.

TABLE II

|  | LEWATIT SPC 108 | SPHEROSIL S | NAFION |
|---|---|---|---|
| Levulose consumed / Levulose introduced % | 24 | 26 | 47 |
| HMF (g) | | | |
| aqueous phase | 60 | — | 80 |
| organic phase | 90 | 20 | 80 |
| Levulinic acid (g) | | | |
| aqueous phase | 0 | 0 | 0 |
| organic phase | 0 | 0 | 0 |
| Humins | 0 | 0 | 0 |
| T % | 21 | 3 | 24 |
| R % | 89 | 11,5 | 50 |

It is observed that the choice of catalyst is important. In particular, it is again noted that the level of by-products is nil whatever the yield obtained.

EXAMPLE 3

Four experiments followed, the first being at atmospheric pressure, the three following ones at a pressure of 5 bars, the atmosphere being respectively:
hydrogen
helium
nitrogen.

The temperature was fixed at 90° C. and the reaction time at 1 hour.

The other conditions were those of Example 1.
The results recorded are grouped in Table III.

TABLE III

|  | Air at P = 1b | $H_2$ P = 5b | He P = 5b | $N_2$ P = 5b |
|---|---|---|---|---|
| Levulose consumed / Levulose introduced % | 32 | 90 | 97 | 92 |
| HMF (g) | | | | |
| aqueous phase | 16 | 120 | 92 | 112 |
| organic phase | 40 | 280 | 188 | 308 |
| Levulinic acid (g) | | | | |
| aqueous phase | 0 | 0 | 0 | 0 |
| organic phase | 0 | 0 | 12 | 10 |
| Humins | 0 | traces | 0 | traces |
| T % | 0 | 57 | 40 | 60 |
| R % | 0 | 63 | 41 | 65 |

On examining the results collected in this Table, the beneficial influence exerted by the pressure on the degree of advance of the reaction although the temperature is kept at 90° C., is noted.

EXAMPLE 4

Into a 50 liters reactor provided with a stirrer and a reflux column, is introduced 33 liters of methylisobutylketone. Successively 1 kg of crystallined levulose and 4 liters of water are added. The levulose dissolves rapidly with stirring in the aqueous phase. Then 0.8 kg of pre-dried cationic resin of the brand "Lewatit SPC 108" is introduced.

The mixture is then brought rapidly to 86° C. and kept to this temperature for ten hours.

Progressively with its formation, the HMF passes into the organic phase (methylisobutylketone) to reach a partition equilibrium. This organic phase being of lower density than that of water, the HMF may be entrained with the solvent by an overflow system. It is then collected in a flask containing 60 liters of methylisobutylketone brought to reflux (127° C.). The temperature not being sufficient for the HMF to be entrained, only the methylisobutylketone vapors are recycled to the reactor. They are condensed and sent by means of a pump into the organic phase to extract the HMF which is formed. They are added to the organic phase before re-enriching the boiler with HMF.

At the end of 10 hours, the aqueous and organic phases of the reactor are separated.

The aqueous phase includes the residual levulose (120 g) as well as a little HMF and levulinic acid.

The organic phase contains the HMF accompanied by very little levulinic acid.

The boiler contains the extracted HMF. The latter is very slightly contaminated with levulinic acid.

After 10 hours of reaction, there was no formation of humins. The amounts of levulinic acid remained small. The amounts of HMF collected were 480 g, which amounts to a conversion ratio T of 68.5% and a yield R in HMF of 78%.

As a result of which and whatever the embodiment adopted, there is thus provided a process for manufacturing HMF whose characteristics emerge sufficiently from the foregoing for it to be unnecessary to dwell further on this subject and which has, with respect to those already existing numerous advantages, especially:

that of reducing the side reactions to a very low level by retarding them, that of enabling a greater reaction speed, that of eliminating the drawbacks due to the corrosion caused by the acid catalysts of the prior art, that of enabling re-cycling of the catalyst.

We claim:

1. Process of manufacturing 5-hydroxymethylfurfural by decomposition of a hexose in a reaction medium comprising water and an organic solvent whose solubility in water is as low as possible, this solvent being selected from among those which are good solvents of HMF, at a temperature situated in the range of 70° to 95° C. in the presence of a solid catalytic support.

2. Process according to claim 1, wherein the temperature is situated in the range of 85° to 90° C.

3. Process according to claim 1, wherein the solvent is selected from among:
ketones
nitriles
ethers
water-immiscible alcohols,
halogenated derivatives,
saturated or unsaturated aliphatic or aromatic hydrocarbons, and
nitroalkanes.

4. Process according to claim 3, wherein
ketones are selected from among methylisobutylketone and diethylketone,
nitriles are selected from among butyronitrile and benzonitrile,
ethers are selected from among dichloroethylethers and dimethoxyethane,
halogenated derivatives are selected from chlorobenzene and dichlorobenzene,
saturated or unsaturated aliphatic or aromatic hydrocarbons are constituted by xylene and
nitroalkanes are selected from among nitromethane and nitropropane.

5. Process according to claim 1, wherein the catalytic support is selected from among cationic resins, super acid resins and solid silica-, alumina- and silica-alumina-based supports functionalised by acid groups.

6. Process according to claim 5, wherein the functionalizing acid groups are sulphonic groups.

7. Process according to claim 1, wherein the reaction is carried out at a pressure above atmospheric pressure and which can reach 100 bars.

8. Process according to claim 7, wherein the pressure is selected in the range from 1 to 5 bars.

9. Process according to claim 1, wherein the HMF formed is extracted continuously from the reaction medium by separating from the aqueous phase the organic solvent phase which has dissolved the HMF, recovering the said HMF from the organic phase, the organic solvent phase from which the HMF has been recovered being recycled into the reaction medium.

10. Process according to claim 1, wherein the hexose applied is solubilised in the aqueous phase in the proportion of 100 to 500 g/l.

* * * * *